United States Patent
Miraftab et al.

(10) Patent No.: US 7,914,889 B2
(45) Date of Patent: *Mar. 29, 2011

(54) WOUND MANAGEMENT FIBRES

(75) Inventors: Moshen Miraftab, Bolton (GB); John Frederick Kennedy, Birmingham (GB); Melanie Rachel Groocock, Stockport (GB); Gill Smart, Bolton (GB)

(73) Assignee: Medlock Medical Limited, Bedfordshire (GB)

( * ) Notice: Subject to any disclaimer, the term of this patent is extended or adjusted under 35 U.S.C. 154(b) by 860 days.

This patent is subject to a terminal disclaimer.

(21) Appl. No.: 10/547,960

(22) PCT Filed: Mar. 8, 2004

(86) PCT No.: PCT/GB2004/000950
§ 371 (c)(1),
(2), (4) Date: Sep. 11, 2007

(87) PCT Pub. No.: WO2004/078063
PCT Pub. Date: Sep. 16, 2004

(65) Prior Publication Data
US 2008/0097001 A1    Apr. 24, 2008

(30) Foreign Application Priority Data
Mar. 7, 2003 (GB) .................................. 0305260.2

(51) Int. Cl.
C08K 7/02 (2006.01)
D02G 3/02 (2006.01)
A61F 13/00 (2006.01)
(52) U.S. Cl. ........ 428/375; 523/105; 523/200; 523/222; 602/48; 604/304
(58) Field of Classification Search ................... 523/200, 523/222, 105; 428/375
See application file for complete search history.

(56) References Cited

U.S. PATENT DOCUMENTS

| | | | | |
|---|---|---|---|---|
| 5,320,903 A | * | 6/1994 | Hirukawa et al. | 428/364 |
| 5,501,711 A | * | 3/1996 | Weltrowski et al. | 8/543 |
| 5,836,970 A | * | 11/1998 | Pandit | 606/213 |
| 6,080,420 A | * | 6/2000 | Qin et al. | 424/443 |
| 6,998,509 B1 | * | 2/2006 | Nielsen | 602/48 |

OTHER PUBLICATIONS

Tamura et al., Preparation of chitosan-coated alginate filament, Materials Science & Engineering C 20 (2002) pp. 143-147.*

* cited by examiner

Primary Examiner — Tae H Yoon
(74) Attorney, Agent, or Firm — Duane Morris LLP

(57) ABSTRACT

A wound management fibre comprising a base fibre having a chitosan material associated therewith, characterised in that the wound management fibre has a significant proportion of chitosan associated therewith.

4 Claims, 3 Drawing Sheets

WOUND MANAGEMENT FIBRES

The present invention relates to wound management fibres.

Fibres are particularly suited to the production of wound management materials as they have a high surface area, a good degree of softness and are easily fabricated into many different forms of products. Fibres made from natural sources, especially polysaccharides, have been considered the most promising materials due to their excellent biocompatibility. Many commercial wound management products (woven and non-woven dressings and hydrogels) are made from such natural polymers and their derivatives. Examples of such products are referred to in the following documents: Kennedy, J. F., Paterson, M., Knill, C. J. and Lloyd, L. L., The diversity of properties of polysaccharides as wound management aids, and characterisation of their structures, In: *Proceedings of the 5th European Conference on Advances in Wound Management*, Cherry, G. W., Gottrup, F., Lawrence, J. C., Moffatt, C. J. and Turner, T. D. (Eds.), Macmillan Magazines Ltd, London, 1996, pp. 122-126; Lloyd, L. L., Kennedy, J. F., Methacanon, P., Paterson, M. and Knill, C. J., Carbohydrate polymers as wound management aids, *Carbohydr. Polym., Special Issue—Gluportwo*, 1998, 37, 315-322; and Kennedy, J. F., Knill, C. J. and Thorley, M., Natural polymers for healing wounds, In: *Recent Advances in Environmentally Compatible Polymers*, Kennedy, J. F., Phillips, G. O. and Williams, P. A. (Eds.), Woodhead Publishing Ltd, Cambridge, 2001, pp. 97-104. The simplest types of wound management materials are retention bandages, support and compression bandages, absorbents, gauzes, tulle dressings, and wound dressing pads produced from woven cellulose fibres (cotton and viscose). Commercial dressings made from cellulose derivatives include Aquacel® (carboxymethyl cellulose, ConvaTec), Comfeel® (carboxymethyl cellulose, Coloplast, available in sheet, powder and pad form), Surgicel® (regenerated cellulose, Johnson & Johnson), and Hydrofibre® (carboxymethyl cellulose, Courtaulds). Commercial alginate-based dressings include Algisite® M (non-woven calcium alginate fibre, Smith & Nephew), Algosteril® (calcium alginate, Beiersdorf), Kaltocarb® (calcium alginate fibre, ConvaTec), Kaltogel® (calcium/sodium alginate gelling fibre, ConvaTec), Kaltostat® (calcium alginate fibres in non-woven pads, ConvaTec), Melgisorb® (calcium/sodium alginate gelling fibre, Molnlycke), Seasorb® (calcium/sodium alginate gelling fibre, Coloplast), Sorbalgon® (calcium alginate, Hartman), and Sorbsan® (calcium alginate fibres in non-woven pads, Maersk). All of which are referred to in Kennedy, J. F., Knill, C. J. and Thorley, M., Natural polymers for healing wounds, In: *Recent Advances in Environmentally Compatible Polymers*, Kennedy, J. F., Phillips, G. O. and Williams, P. A. (Eds.), Woodhead Publishing Ltd, Cambridge, 2001, pp. 97-104; and *British National Formulary*, Pharmaceutical Press, London, 41, March 2001.

Among the various fibrous and hydrogel products, alginate products are currently the most popular products used in wound management. For example, Jarvis P. M., Galvin D. A. J., Blair S. D. and McCollum C. N., *Thromb. Haemostas.*, 1987, 58, 80; and Atwood, A. I., *Br. J. Plastic Surg.*, 1989, 42, 373-379 report that alginate products have haemostatic properties and may enhance the rate of healing of skin wounds.

Another type of natural polysaccharide, which has attracted the attention of academic institutions and industry, is chitin, and its partially deacetylated derivative, chitosan. For example, Balassa, L. L. and Prudden, J. F., Applications of chitin and chitosan in wound-healing acceleration, In: *Proceedings of The First International Conference on Chitin/Chitosan*, Muzzarelli, R. A. A. and Pariser, E. R. (Eds.), Massachusetts Institute of Technology Sea Grant Report, 1978, MTTSG 78-7, pp. 296-305; Technical textiles, a special survey, *Textile Horizons*, October, 1995, 26-33; and Muzzarelli, R. A. A., Mattioli-Belmonte, M., Pugnaloni, A. and Biagini, G., Biochemistry, histology and clinical uses of chitins and chitosans in wound management, In: *Chitin and Chitinases*, Jollès, P. and Muzzarelli, R. A. A. (Eds.), Birkhäuser Verlag, Basel, 1999, pp. 251-264 report that the presence of chitin/chitosan in a dressing can promote the growth of fibroblasts and accelerate the wound management process, making it one of the most promising materials in wound management products. Chitins and chitosans are used in a wide variety of commercial application areas, such as cosmetics, haemostatic agents, drug delivery vehicles, wound dressings, etc. as exemplified in Skjak-Braek, G., Anthonsen, T. and Sandford, P. (Eds.), *Chitin and Chitosan: Sources, Chemistry, Biochemistry, Physical Properties and Applications*, Elsevier Applied Science, New York, 1989; *Chitin and Chitosan*, Reports Group, Technical Insights, Wiley, Englewood, N.J., 1989; and Muzzarelli, R. A. A., Biagini, G., Damadei, A., Pugnaloni, A. and Da Lio, J., Chitosans and other polysaccharides as wound dressing materials, In: *Biomedical and Biotechnological Advances in Industrial Polysaccharides*, Crescenzi, V., Dea, I. C. M., Paoletti, S., Stivala, S. S. and Sutherland, I. W. (Eds.), Gordon and Breach, Amsterdam, 1989, pp. 77-88. However, due to the high costs of the raw materials wound dressing products made from pure chitosan fibres are not commercially viable, particularly raw materials of suitably high purity. Furthermore, poor textile processing properties of the resulting fibres is a major problem, although some efforts have been made recently in the production and application of fibrous wound dressings prepared using chitosan by wet laid matt processing. Production of chitosan/alginate fibres cannot be achieved by standard direct polymer blend methods as chitosan and alginate form gels when mixed together in solution.

Attempts to harness the properties of both the alginate and chitin/chitosan materials have been made by Tamura, H. et al., *Mat. Sci. Eng.*, 2002, C 20, 1-2, 143-147, for example. This document describes the preparation of alginate filaments coated with chitosan. The method of preparation involves passing fibres through a coagulation bath comprising chitosan and calcium chloride. Ethanol is used to dry the resulting coated filament. Chitosan is known to precipitate from solution in the presence of calcium ions and this known method described provides alginate filaments that are typically coated with insubstantial amounts of chitosan. Thus, the coated filaments described by Tamura have some inferior physical properties and will have greatly reduced biological efficacy.

An object of the present invention is to improve the incorporation of chitosan as coating on/absorption into base fibres such as alginate.

According to a first aspect of the present invention there is provided a wound management fibre comprising a base fibre having a chitosan material associated therewith, characterised in that the wound management fibre has a significant proportion of chitosan associated therewith.

Chitosan preferably comprises from 1 to 30% by weight of the total wound management fibre.

Advantageously the wound management fibres described herein have enhanced physical properties. Furthermore, the wound management fibres described herein have an increased chitosan content relative to prior art systems and will have increased biological efficacy relative to prior art systems.

The wound management fibres described herein may be fabricated into a wide variety of wound management materials such as dressings, gauzes, wound dressing pads and the like.

The base fibre of the present invention may comprise any biodegradable polymeric material and preferably comprises alginate polymer. Alginate is composed of mannuronate (M) and guluronate (G) monomeric units, as shown below.

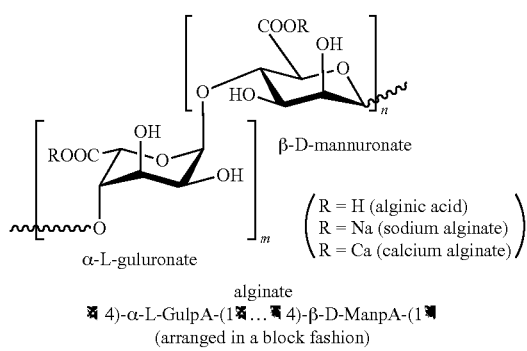

alginate
⫪4)-α-L-GulpA-(1⫪...⫪4)-β-D-ManpA-(1⫪
(arranged in a block fashion)

By chitosan it is meant chitosan per se, chitin (fully N-acetylated, only n units as in chitin figure below) and chitan (fully N-acetylated, only m units in chitosan figure below) and close derivatives and salts thereof. The monomeric units of chitin and chitosan are shown below.

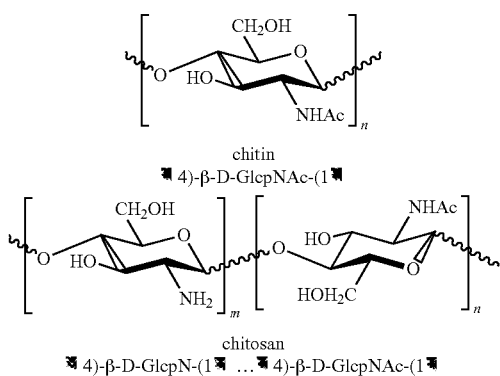

chitin
⫪4)-β-D-GlcpNAc-(1⫪ chitosan
⫪4)-β-D-GlcpN-(1⫪ ...⫪4)-β-D-GlcpNAc-(1⫪

The chitosan of the present invention may be acetylated or deacetylated to any degree. By acetylation it is meant the presence of or addition of N-acetyl groups and by deacetylation it is meant the absence or removal of N-acetyl groups. The degree of acetylation (DA) is the average number of acetyl groups per monomeric unit i.e. a DA of 0.1 means one out of every 10 GlcN residues is acetylated. Chitin has a DA of 1. The degree of deacetylaytion (DD) is the average number of free amino groups per monomeric unit, i.e. a DD of 0.1 means every 9 out of 10 GlcN units is acetylated. Acetylation and deacetylation can also be expressed as a percentage of the total groups present.

The nature of the chitosan of the present invention is chosen largely out of consideration for the required properties of the wound management fibre.

That said, the chitosan of the present invention preferably has a DD greater than 70%.

Advantageously the cationic nature of the chitosan of the present invention is enforced. This gives the opportunity of a strong interaction with the anionic alginate.

As referred to previously, a further advantage of the present invention is that the wound management fibre produced has a higher content of chitosan associated therewith than is the case with prior art systems. This increased content may be achieved or facilitated by enhanced penetration of and/or binding to the base fibre which can be achieved by disrupting the polymeric structure of the chitosan prior to its application to the base fibre. This disruption gives rise to chitosan which is composed of a plurality of chitosan fragments which have a range of reduced molecular weights relative to the undisrupted chitosan.

Thus, according to a second aspect of the present invention there is provided a wound management fibre comprising a base fibre having chitosan associated therewith, characterised in that the chitosan is disrupted to provide chitosan fragments of reduced molecular weight.

Preferably, the chitosan fragments have a reduced molecular weight in the range from 1 to 150 kDa.

Advantageously this disruption provides wound management fibres with similar physical properties and an increased rate of biological efficacy. The chitosan fragments are able to penetrate the base fibre more readily increasing the chitosan loading in the fibres and ultimate delivery to a wound.

Disruption may be effected by any suitable means, for example, biological means (enzymatic cleavage), radiolytic means and chemical means. In a particularly preferred embodiment it is effected by hydrolytic means.

Hydrolysis of the chitosan material may be achieved by treatment with alkali, but is preferably achieved by treatment with acid.

Disruption of the chitosan is effected to a significant extent.

The chitosan may provide an outer coating layer for the base fibre or it may penetrate the base fibre to at least an extent or the chitosan may penetrate the base fibre to an extent whilst at the same time providing an outer coating layer. The molecular orientation of the chitosan relative to the base fibre may be affected by the degree of depolymerisation that the chitosan has undergone.

According to a third aspect of the present invention there is provided a wound management fibre comprising a base fibre having a chitosan material associated therewith characterised in that a significant amount of chitosan penetrates the base fibre.

Base fibres of the present invention are preferably made by acid precipitation in the absence of calcium ions, since the presence of calcium ions results in a dramatic reduction in the amount of chitosan associated with the fibre.

Thus, according to a fourth aspect of the present invention there is provided a method for the production of a wound management fibre comprising the steps of: extruding a base fibre, treating said base fibre with a chitosan material so as the chitosan material forms an association with the base fibre, characterised in that the base fibre is treated with the chitosan material in the absence of free calcium ions.

According to a fifth aspect of the present invention there is provided a method for the production of a wound management fibre comprising the steps: extruding a base fibre, treating the base fibre with a chitosan material so as the chitosan material forms an association with the base fibre, characterised in that the chitosan is disrupted prior to the treatment of the base fibre such that the chitosan comprises chitosan fragments of reduced molecular weight.

In order that the base fibre has sufficient chitosan associated therewith the base fibre is treated with chitosan material having a chitosan concentration preferably in the range from 2.5 to 5.0% w/v and most preferably in the range from 3.0 to 4.0% w/v.

The various aspects of the invention may be in any combination and the base fibre may be any alginate or other suitable carbohydrate polymer.

In a preferred embodiment, the wound management fibre of the present invention is prepared using a multi-functional laboratory extruder. The extruder essentially comprises an upright wet extruder comprising a plurality of baths positioned one above the other. The alginate base fibre is prepared from a spinning dope which is pumped, under pressure, through a spinneret. The spinneret is located in a first bath, i.e. a coagulation bath containing an aqueous solution of hydrochloric acid. Alginate fibres are drawn from the spinneret by way of a first set of rollers. Coagulation of the fibres occurs as the fibres are drawn submersed in the aqueous hydrochloric acid solution. From the first bath the fibres pass into a second bath containing water via a second set of rollers. The water simply washes any acid residue from the fibre. From the second bath the fibres pass, via a third set of rollers, into a third bath containing chitosan. The chitosan may or may not have undergone a depolymerisation process prior to addition to the third bath. The fibres pass through the third bath and through a fourth set of rollers in order to squeeze out excess liquid. Finally, the fibres are dried by way of aqueous extraction/solvent evaporation. The solvent may be any suitably volatile solvent such as acetone. Following drying the fibre is wound for transport and/or further processing.

In an alternative embodiment the first bath further comprises calcium chloride, in order to produce the calcium salt of the alginate. These calcium ions remain ionically bonded to the alginate fibre, but any migration of them would play a part in any subsequent process steps.

The plurality of baths may be positioned in any suitable orientation.

The physical properties of the wound management fibres described herein can be quantified with reference to the draw ratio, the elongation and the tenacity of the fibres.

The Draw Ratio (or stretch ratio) is the ratio of the speeds of the first and second rollers as referred to in FIG. 1. The draw ratio provides an indication of the amount of stretching a fibre undergoes during its production, and is defined as:

$$DR = \left(\frac{S_2}{S_1}\right)$$

where:

$DR$ = Draw Ratio $S_1$ = speed of $1^{st}$ roller $S_2$ = speed of $2^{nd}$ roller (clearly $S_1$ and $S_2$ must be in the same speed units)

Elongation or extension describes the length by which a fibre extends when a load is applied. As the load is increased the elongation increases until the fibre breaks (under a specific load). The % elongation is determined from the ratio of the break length to the original length as indicated below:

$$\% \text{ Elongation} = \left(\frac{l_b}{l_0}\right) \times 100$$

where:

$l_b$ = break length $l_o$ = original length (clearly $l_b$ and $l_o$ must be in the same length units)

Tenacity defines fibre strength with respect to its linear density:

$$\text{Tenacity} = \left(\frac{L_b}{D_L}\right)$$

where:

$L_b$ = break load $(N)$ $D_L$ = linear density $(tex)$

Linear density is described in units of tex, which is the weight of fibre in g per 1000 m length. Thus, 1 dtex is the weight in g per 10000 m length of fibre.

Preferably, the tenacity of the fibres described herein is in the range of 1-6 cN/dtex.

The present invention will now be described further by way of example only and with reference to the following drawing:

BRIEF DESCRIPTION OF THE DRAWINGS

FIG. 1 shows a laboratory extruder 1 comprising a first 2, second 3 and third 4 bath positioned substantially one above the other. The extruder 1 further comprises a dope tank 5 containing a base fibre spinning dope. The spinning dope is pumped, under pressure, through a spinneret 6 located in the first bath 2. Base fibres 7 are drawn from the spinneret 6 via a set of rollers 8, said rollers also being located in the first bath 2. As the fibres are drawn they pass through an acid medium 9 contained within the first bath 2. The fibres 7 travel from the first bath 2 to a second bath 3 in a substantially vertical manner via a second set of rollers 10. The fibres 7 pass through the second bath 3, the second bath 3 containing water. Passage of the fibres 7 through the second bath 3 is facilitated by rollers 11a and 11b located in the bath 3. The fibres 7 travel from the second bath 3 to a third bath 4 via a third set of rollers 13. The fibres 7 pass through the third bath 3, the third bath containing a chitosan solution 14. Passage of the fibres 7 through the third bath 4 is facilitated by rollers 12a and 12b located in the bath 4. The fibres 7 then leave the third bath 4 and pass through a fourth set of rollers 15 in order to remove excess liquid. After passing through the fourth set of rollers 15 the fibres 7 are dried (not shown).

FIG. 2 shows the effect of the chitosan bath concentration and hydrolysis time on mean fibre chitosan content. It can be seem that a hydrolysis time of between 3 and 15 hours results in chitosan being associated with the fibre. However, the concentration of the chitosan used to treat the base fibre is also important. In order to achieve a mean chitosan content greater than 8% w/v the chitosan concentration should be greater than 2% w/v and the hydrolysis time should be at least 6 hours.

FIG. 3 shows that following treatment with a chitosan solution having a chitosan concentration of 9% w/v and wherein the chitosan has undergone hydrolysis for 12 hours the fibre 16 is fully penetrated with chitosan 17.

FIG. 4 shows how base fibres produced using a chitosan solution having a chitosan concentration of 3.0% w/v and wherein the chitosan has been hydrolysed for between 3 and 15 hours release the chitosan associated therewith after incubation periods of between 1 and 48 hours.

The laboratory extruder of the present invention is not limited to the above orientation, for example the baths may be positioned next to each other in a substantially horizontal manner.

The present invention will now be described further by way of example only and with reference to the following examples:

Examples 1 to 4 describe fibre processing techniques and parameters used to produce the fibres of the present invention. Table 1 shows polymeric materials used to produce the fibres.

EXAMPLE 1

Unified Fibre Spinning Conditions

Figure 4:
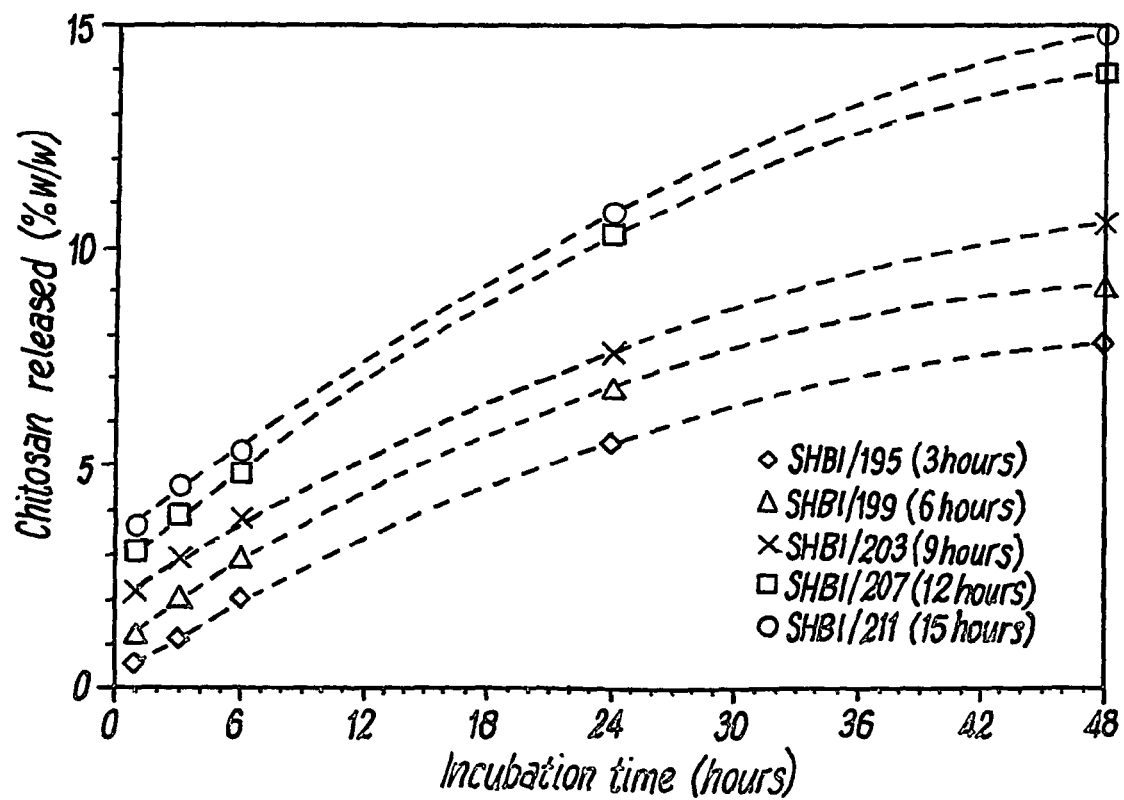
FIG. 4 is a graph showing how chitosan is released from a fibre at varying incubation periods.

Fibre spinning is conducted using a conventional wet spinning technique (as detailed in FIG. 4 and described previously). The spinning dope solution of sodium alginate (1-6% w/v, depending on type and viscosity), or any other water soluble alginate, is extruded into a coagulation bath containing either hydrochloric acid (0.2M) and/or calcium chloride (1-3% w/v) to afford the corresponding alginic acid and/or calcium alginate fibres. The resultant fibres are then passed through a series of water washing baths, before being passed through a treatment bath containing chitosan (0-5% w/v, unhydrolysed or hydrolysed (the hydrolysis procedure is detailed below in Example 2)). The resultant alginate/chitosan fibre is squeezed to remove excess liquid, and is then treated with acetone solutions of increasing acetone concentration (50-100% v/v) to remove water. The resultant fibres are separated by hand and are conditioned at room temperature for 24 hours.

EXAMPLE 2

Production of a Chitosan Hydrolysate

Chitosan (6.1 g, excl. moisture) is dissolved in deionised water (150 mL) and acetic acid (1.5 mL). The solution is stirred until a viscous clear solution is obtained (this takes ~3-4 hours). Hydrochloric acid (5 mL) is added and vigorous stirring is applied until a homogenous solution is obtained. The resulting solution is heated under reflux (2-24 hours), cooled, filtered to remove any insoluble material, and is ready for use in a coagulation bath (this solution being 3.9% w/v based on initial chitosan loading). Coagulation bath contents of different chitosan concentrations are prepared by simply altering the initial amount of chitosan used accordingly. Similar proportions of materials are employed for the production of larger volumes.

EXAMPLE 3

Optimum Fibre Spinning Conditions

The spinning dope solution of sodium alginate (6% w/v) is extruded into a coagulation bath containing hydrochloric acid (0.2M) to afford the corresponding alginic acid fibre. The resultant fibres are then passed through a water washing bath before being passed through a treatment bath containing hydrolysed chitosan (3.9% w/v). The resultant chitosan/alginic acid fibre is squeezed to remove excess liquid then washed with acetone solution of increasing acetone concentration (50-100% v/v) to remove water. The fibre is left to condition at room temperature for 24 hours.

EXAMPLE 4

Fibre Analysis/Characterisation

All produced fibres were subjected to a range of analyses to determine their composition, mechanical properties, and antibacterial efficacy. The moisture, ash, sodium (and in some cases calcium), and nitrogen contents of all fibres (on a % weight basis) were determined. This allowed the chitosan content of each fibre to be determined from its nitrogen content (based on the nitrogen contents of the 100% alginate fibre and chitosan used in its production). The physical properties measured were % elongation, and tenacity.

Table 1 shows various materials used to produce the fibres described in the examples;

TABLE 1

| Code | Material | Supplier | Viscosity (mPa·s, 1% soln.) | Comments |
|---|---|---|---|---|
| Sodium Alginates | | | | |
| A1 | Protanal LF 10/60 | Pronova | spec. 20-70 batch ~34 | ManA 25-35% GulA 65-75% |
| A2 | Manucol ® DH | ISP Alginates | 40-90 | — |
| A3 | Manugel ® GMB | ISP Alginates | 110-270 | — |
| Chitosans | | | | |
| C1 | TM 370 | Primex | 150 (in 1% AcOH) | DD 88% |
| C2 | Seacure 443 | Pronova | — | — |
| C3 | Seacure CL 310 | Pronova | 200-800 | chitosan.HCl |
| C4 | Kate II | Kate Int. | 50-100 (in 1% AcOH) | DD > 85% |

By way of illustration of the foregoing examples, a variety of data specific to the said examples is provided and discussed.

The data in Table 2 for chitosan/calcium alginate fibres prepared using the prior art methodology (samples 1 and 2) is in close agreement with that stated in the prior art. However, the chitosan/alginate fibres produced using the methodology detailed herein show a significantly higher level of non-disrupted chitosan incorporation (sample 3). Samples 4 and 5 are the control fibres prepared from 100% alginate and chitosan respectively.

The results illustrated in table 2 demonstrate that the method of the present invention results in a significant increase in non-disrupted chitosan incorporation, compared with prior art.

TABLE 2

| Sample No. | Dope | Draw Ratio | 1st Bath | 2nd Bath | 3rd Bath | Moisture (% w/w) | Ash (% w/w) | Na (% w/w) | Ca (% w/w) | Chitosan (% w/w) | Elongation (%) | Tenacity (cN/dtex) |
|---|---|---|---|---|---|---|---|---|---|---|---|---|
| 1 | A1 (1%) | 1.18 | CaCl$_2$ (3%) + C4 (0.014%) | CaCl$_2$ (3%) | — | 12.8 | 22.0 | 0.04 | 8.4 | <0.2 | 4.5 | 1.9 |
| 2 | A1 (1%) | 1.18 | CaCl$_2$ (3%) + C4 (0.067%) | CaCl$_2$ (3%) | — | 12.6 | 22.7 | 0.03 | 8.6 | <0.2 | 3.6 | 2.5 |
| 3 | A1 (6%) | 1.27 | HCl (0.2M) | water | C1 (3.9%) | 10.2 | 1.7 | 0.05 | — | 10.4 | 16.8 | 2.1 |
| 4 | A1 (6%) | 1.18 | HCl (0.2M) | water | — | 5.4 | 1.4 | 0.08 | — | 0 | 20.4 | 2.2 |
| 5 | C1 (6%) | 1.22 | NaOH (2%) | — | — | 1.0 | <1 | 0.02 | — | 100 | 16.2 | 2.2 |

The different (in terms of viscosity, molecular weight, composition, etc) sodium alginate and chitosan starting materials obtained (as detailed in Table 1) were used to produce a range of alginic acid fibres, which were subsequently subjected to different chitosan treatments. Variables included sodium alginate type, method of alginic acid fibre production (washed and unwashed), and non-disrupted chitosan type. The results of the analyses (chemical and physical) of these fibres are detailed in Table 3.

fibres had to be produced at a draw ratio of 1.09 (compared with 1.18 for A1) to avoid fibre filament breakage. In general, water washing resulted in better fibres (in terms of both physical properties and chitosan contents).

It was postulated that the use of a disrupted chitosan may result in higher levels of chitosan incorporation into the alginate fibre, since fragments (i.e. molecules of lower molecular size than the parent non-disrupted chitosan molecules) should be able to more easily penetrate the alginate fibre structure.

TABLE 3

| Dope (% w/w) | Draw Ratio | 1st Bath | 2nd Bath | 3rd Bath | Moisture (% w/w) | Ash (% w/w) | Na (ppm) | Chitosan (% w/w) | Elongation (%) | Tenacity (cN/dtex) |
|---|---|---|---|---|---|---|---|---|---|---|
| A1 (6%) | 1.18 | HCL (0.2M) | water | C2 (2%) | 11.2 | 1.6 | 720 | 0.7 | 29.1 | 1.4 |
| A1 (6%) | 1.18 | HCL (0.2M) | water | C3 (3.2%) | 12.5 | 0.7 | 540 | 2.1 | 23.4 | 2.0 |
| A1 (6%) | 1.18 | HCL (0.2M) | — | C2 (2%) | 11.6 | 1.0 | 710 | 1.1 | 12.5 | 1.0 |
| A1 (6%) | 1.18 | HCL (0.2M) | — | C3 (3.2%) | 12.3 | 0.4 | 490 | 1.1 | 15.0 | 1.0 |
| A2 (6%) | 1.09 | HCL (0.5M) | water | C2 (2%) | 11.2 | 1.0 | 500 | 1.7 | 4.8 | 0.6 |
| A2 (6%) | 1.09 | HCL (0.5M) | water | C3 (3.2%) | 11.6 | 0.8 | 530 | 5.5 | Tb | tb |
| A2 (6%) | 1.09 | HCL (0.5M) | — | C2 (2%) | 11.3 | 0.8 | 890 | 2.3 | 10.9 | 1.1 |
| A2 (6%) | 1.09 | HCL (0.5M) | — | C3 (3.2%) | 11.4 | 0.7 | 750 | 0.9 | Tb | tb |
| A3 (4%) | 1.09 | HCL (0.2M) | water | C2 (2%) | 11.4 | 1.1 | 520 | 2.3 | 10.5 | 0.7 |
| A3 (4%) | 1.09 | HCL (0.2M) | water | C3 (3.2%) | 12.4 | 1.2 | 350 | 2.8 | Tb | tb |
| A3 (4%) | 1.09 | HCL (0.2M) | — | C2 (2%) | 12.3 | 0.9 | 780 | 0 | Tb | tb |
| A3 (4%) | 1.09 | HCL (0.2M) | — | C3 (3.2%) | 12.1 | 0.8 | 720 | 1.1 | Tb | tb |

(tb = too brittle to test)

The chitosan/alginate fibres produced from alginate A1 had significantly better physical properties than those fibres produced from both A2 and A3. This is because A2 required a higher acid strength to produce a fibre (0.5M compared with 0.2M for A1 and A3), A3 had to be used at a concentration of 4% (since 6% was too viscous to use), and both A2 and A3

Initially, a single chitosan (C1) was subjected to controlled hydrolysis (detailed previously in Example 2). Alginic acid fibres (produced from alginate A1) were passed through a coagulation bath containing the disrupted chitosan (C1, 3.9%). The results of the analyses (chemical and physical) of these fibres are detailed in Table 5.

TABLE 4

| Dope (% w/w) | Draw Ratio | 1st Bath | 2nd Bath | 3rd Bath | Moisture (% w/w) | Ash (% w/w) | Na (ppm) | Chitosan (% w/w) | Elongation (%) | Tenacity (cN/dtex) |
|---|---|---|---|---|---|---|---|---|---|---|
| A1 (6%) | 1.27 | HCl (0.2M) | water | hydrol. C1 (3.9%) | 7.9 | 1.2 | 100 | 13.7 | 14.8 | 2.4 |

TABLE 4-continued

| Dope (% w/w) | Draw Ratio | 1st Bath | 2nd Bath | 3rd Bath | Moisture (% w/w) | Ash (% w/w) | Na (ppm) | Chitosan (% w/w) | Elongation (%) | Tenacity (cN/dtex) |
|---|---|---|---|---|---|---|---|---|---|---|
| A1 (6%) | 1.18 | HCl (0.2M) | water | hydrol. C1 (3.9%) | 6.4 | <1 | 130 | 15.4 | 20.6 | 2.6 |
| A1 (6%) | 1.18 | HCl (0.2M) | — | hydrol. C1 (3.9%) | 8.2 | <1 | 210 | 13.4 | 14.8 | 2.0 |

The data presented in Table 4 clearly demonstrates that the use of disrupted chitosan results in a significant increase in the level of chitosan incorporation into the fibre and improved fibre physical properties (compared with the data for non-disrupted chitosan presented previously in Table 2). With hydrolysed chitosan, the absence of water washing appeared to result in a slight reduction in the resultant chitosan content of the fibre.

Treatment with disrupted chitosan results in significant increases in both fibre tenacity and more importantly, fibre chitosan content.

A selection of different chitosans were subsequently hydrolysed (C2-4) under the same conditions and were used to treat a range of alginic acid fibres produced from the three different sodium alginate samples discussed previously (A1-3). Therefore, variables included sodium alginate type, method of alginic acid fibre production (acid concentration, water washed and unwashed), and disrupted chitosan type and concentration. The results of the analyses (chemical and physical) of these fibres are detailed in Table 5.

Several other hydrolysed chitosans were also produced and evaluated, namely from Kitosan (A. & E Connock, Cosmetic Grade), Type 222 chitosan (France-Chitine, high viscosity), and Type 242 chitosan (France-Chitine, high purity). However, all of the fibres produced using these hydrolysed chitosans were too weak/brittle for physical testing.

The best fibres (in terms of both chitosan incorporation and physical properties) were produced using alginic acid fibres produced from sodium alginate A1 (6%) using a hydrochloric acid (0.2M) coagulation bath and a draw ratio of 1.18, and subsequent treatment of the produced fibres with disrupted chitosan C4 (3.9%).

Chitosan Location

In order to establish how chitosan is incorporated into base fibres ninhydrin staining was used to detect the presence of chitosan in the produced fibres. It is noted that the intensity of the staining tends to increase with increasing concentrations of chitosan. Cross sections of fibres produced using a chitosan solution having a chitosan concentration of 3 to 4% w/v were examined.

Figure 1:
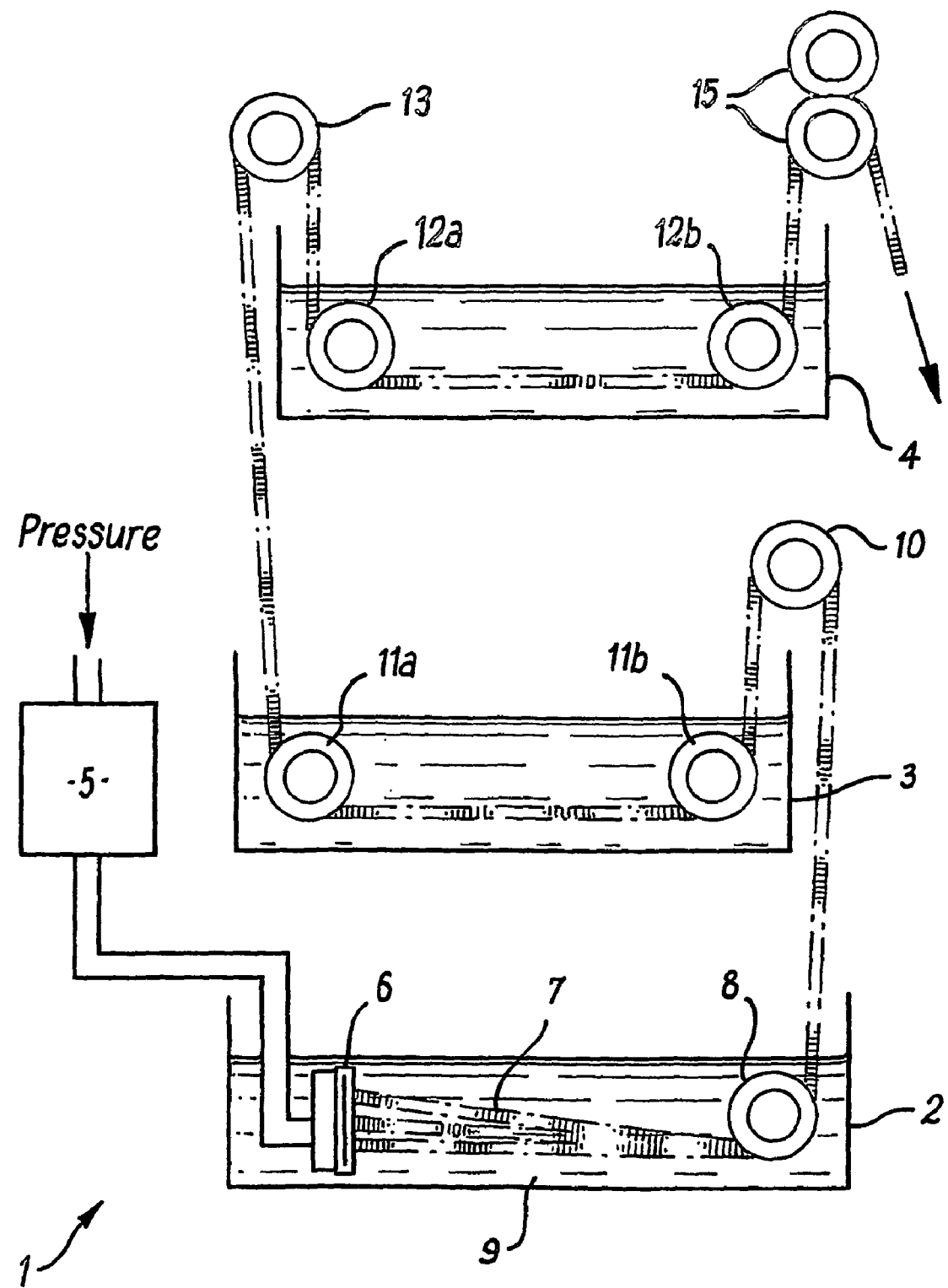
FIG. 1 is a schematic representation of one embodiment of the method of the present invention.
Figure 2:
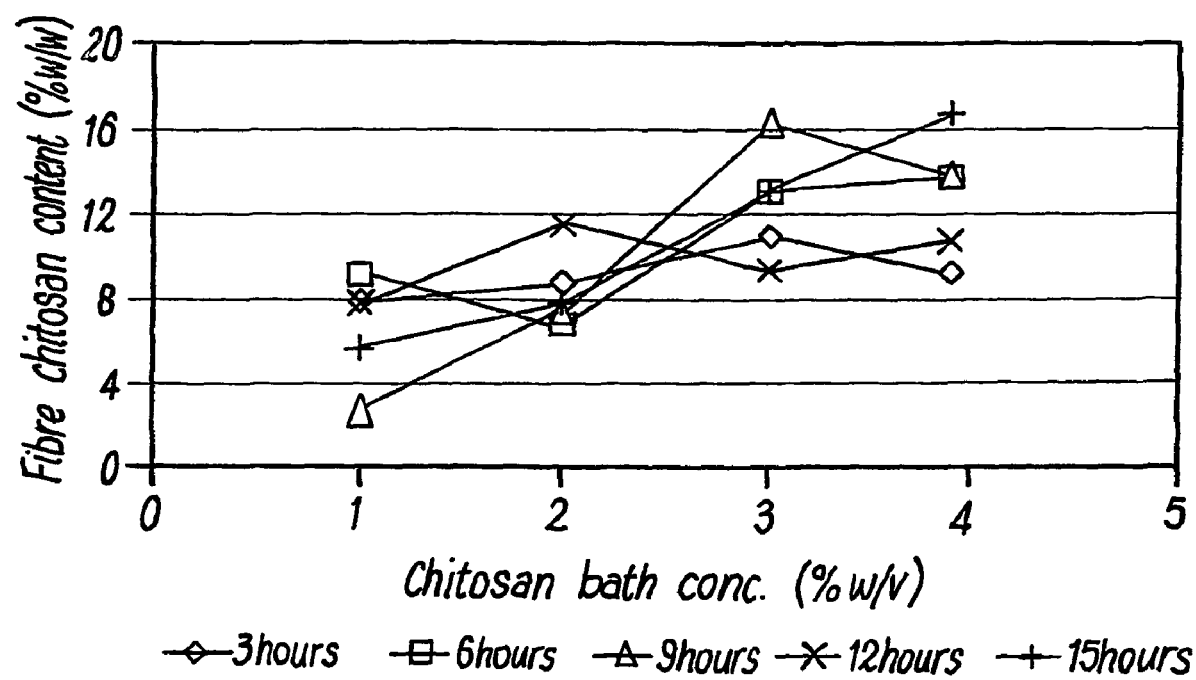
FIG. 2 is a graph showing the effect of chitosan bath concentration and hydrolysis time on mean base fibre chitosan content.
Figure 3:
FIG. 3 is a representation of microscopic analysis showing the degree to which chitosan has penetrated a base fibre.

With chitosan solutions having a 3% w/v chitosan concentration and using 3 hours of hydrolysis, very little if any sign of staining is present indicating little if any chitosan penetrates the fibre. With 6 hours hydrolysis the breakdown of chitosan molecules into smaller fragments appears to be taking place and penetration of the chitosan into the alginate core appears to be occurring. With 9 hours of hydrolysis the cross sections increasingly show more prominent staining and in some parts entire cross sections are fully stained indicating that surface deposits are dominant in some fibres but full penetration has occurred in others. Once hydrolysis is increased to 12 or 15 hours staining is less effective and marginally less chitosan deposits are detected on fibre cross sections. However some fibres still show full penetration as illustrated in FIG. 3.

Release of Chitosan from the Fibre

In order to determine how fibres which have been penetrated by chitosan then release that chitosan, incubation experiments were conducted. Base fibres produced using a chitosan solution having a chitosan concentration of 3% w/v and wherein the chitosan was hydrolysed for between 3 and 15 hours were incubated for between 1 and 48 hours. The amount of chitosan released therefrom was calculated as a percentage of the original weight of the fibre and the results are shown in FIG. 4.

FIG. 4 shows that fibres produced from increasing hydrolysis conditions release chitosan more readily. This may be an interesting phenomenon for a wound dressing which may wish to impart chitosan to the wound for its antibacterial or other properties.

TABLE 5

| Dope (% w/w) | Draw Ratio | 1st Bath | 2nd Bath | 3rd Bath | Moisture (% w/w) | Ash (% w/w) | Na (% w/w) | Chitosan (% w/w) | Elongation (%) | Tenacity (cN/dtex) |
|---|---|---|---|---|---|---|---|---|---|---|
| A1 (6%) | 1.18 | HCl (0.2M) | water | hydrol. C2 (2%) | 11.7 | 0.1 | 0.026 | 11.9 | 29.3 | 2.7 |
| A1 (6%) | 1.18 | HCl (0.2M) | water | hydrol. C3 (3.2%) | 11.9 | 0.3 | 0.033 | 7.4 | 20.5 | 2.5 |
| A2 (6%) | 1.18 | HCl (0.5M) | water | hydrol. C2 (2%) | 11.7 | 0.3 | 0.032 | 16.3 | 10.9 | 1.8 |
| A2 (6%) | 1.18 | HCl (0.5M) | water | hydrol. C3 (3.2%) | 11.8 | 0.3 | 0.045 | 9.6 | 5.6 | 1.2 |
| A3 (4%) | 1.09 | HCl (0.2M) | water | hydrol. C2 (2%) | 11.4 | 0.4 | 0.026 | 10.1 | 6.0 | 0.7 |

TABLE 5-continued

| Dope (% w/w) | Draw Ratio | 1st Bath | 2nd Bath | 3rd Bath | Moisture (% w/w) | Ash (% w/w) | Na (% w/w) | Chitosan (% w/w) | Elongation (%) | Tenacity (cN/dtex) |
|---|---|---|---|---|---|---|---|---|---|---|
| A3 (4%) | 1.09 | HCl (0.2M) | water | hydrol. C3 (3.2%) | 11.8 | 0.4 | 0.030 | 8.8 | 7.3 | 0.8 |
| A2 (6%) | 1.18 | HCl (0.5M) | water | hydrol. C4 (1%) | 10.9 | 0.5 | — | 20.7 | tw | tw |
| A2 (6%) | 1.18 | HCl (0.5M) | water | hydrol. C4 (2%) | 11.4 | 0.6 | — | 15.5 | tw | tw |
| A2 (6%) | 1.18 | HCl (0.5M) | water | hydrol. C4 (3.9%) | 11.9 | 0.1 | — | 22.0 | 10.1 | 1.4 |
| A1 (6%) | 1.18 | HCl (0.2M) | water | hydrol. C4 (1%) | 10.5 | 0.5 | 0.040 | 2.0 | 25.0 | 2.1 |
| A1 (6%) | 1.18 | HCl (0.2M) | water | hydrol. C4 (2%) | 9.9 | 0.7 | 0.060 | 5.4 | 15.5 | 1.5 |
| A1 (6%) | 1.18 | HCl (0.2M) | water | hydrol. C4 (3%) | 10.7 | 0.4 | 0.030 | 14.7 | 19.2 | 1.5 |
| A1 (6%) | 1.18 | HCl (0.2M) | water | hydrol. C4 (3.9%) | 10.5 | 0.9 | 0.030 | 21.2 | 35.6 | 1.8 |
| A1 (6%) | 1.18 | HCl (0.2M) | water | hydrol. C4 (5.0%) | 10.1 | 1.0 | 0.030 | 25.2 | tb | tb |

(tw = too weak to test);
(tb = too brittle to test)

A wide range of control fibres were also produced and analysed. These included pure alginic acid and calcium alginate fibres (produced from A1-A3), pure chitosan fibres (produced from C1-C4), and a range of alginic acid fibres treated with glucosamine hydrochloride (GlcN.HCl, 3.9%), N-acetyl-D-glucosamine (GlcNAc, 3.9%), a 0% chitosan bath (i.e. the hydrolysis reagents) and a dialysed hydrolysed chitosan (i.e. the hydrolysis reagents removed).

Hydrolysed chitosan (C4, 3.9%) was also used to treat calcium alginate fibres produced using a calcium chloride coagulation bath and alginic acid/calcium alginate fibres produced using a hydrochloric acid/calcium chloride coagulation bath. The results of the analyses of these fibres are presented in Table 6. These results show that the presence of calcium/absence of HCl in the 1st coagulation bath reduces the level of chitosan incorporation into the fibre (Table 5: fibre produced using the same materials/conditions except without any calcium in the 1st bath has a chitosan level of ~21% w/w).

with different disrupted and non-disrupted chitosans suggest that chitosans with a high DD (>70%) produce better fibres.

TABLE 7

| Chitosan | $M_p$ (kDa) | $M_n$ (kDa) | $M_w$ (kDa) | $M_z$ (kDa) | d | DA |
|---|---|---|---|---|---|---|
| Unhydrolysed Chitosans: | | | | | | |
| C2 | 888 | 210 | 1215 | 2938 | 5.8 | 0.33 |
| C3 | 448 | 134 | 698 | 1921 | 5.2 | — |
| C4 | 697 | 144 | 993 | 2667 | 6.9 | 0.20 |
| Hydrolysed Chitosans: | | | | | | |
| C2 | 14.8 | 6.6 | 18.1 | 36.9 | 2.7 | 0.26 |
| C3 | 5.5 | 4.1 | 8.4 | 16.4 | 2.0 | — |
| C4 | 17.7 | 7.3 | 32.3 | 121.2 | 4.4 | 0.14 |

$M_p$ is simply the peak molecular weight. $M_n$ is the number-average molecular weight and is simply the arithmetic mean,

TABLE 6

| Dope (% w/w) | Draw Ratio | 1st Bath | 2nd Bath | 3rd Bath | Moisture (% w/w) | Ash (% w/w) | Na (% w/w) | Ca (% w/w) | Chitosan (% w/w) | Elongation (%) | Tenacity (cN/dtex) |
|---|---|---|---|---|---|---|---|---|---|---|---|
| A1 (6%) | 1.18 | CaCl$_2$ (2%) | water | hydrol. C4 (3.9%) | 12.8 | 8.6 | 0.03 | 3.32 | 0.0 | 7.2 | 4.4 |
| A1 (6%) | 1.18 | HCl (0.2M) CaCl$_2$ (1%) | water | hydrol. C4 (3.9%) | 10.9 | 2.9 | 0.04 | 1.02 | 3.8 | 10.3 | 1.8 |

Characterisation of the different chitosan starting materials utilised, and the produced disrupted chitosan, was performed (in terms of molecular size and degree of acetylation), in order to more fully explain the observed results presented herein. Selected obtained information is provided in Table 7. From this data (and data in previous tables), the results obtained i.e. the sum of the molecular weights of all the molecules divided by the total number of molecules. $M_w$ is the weight-averaged molecular weight, i.e. the weighted mean, and is the sum of the molecular weight squared of all the molecules divided by the total molecular weight of all the molecules. Further increasing the weighting of the average gives rise to the z average. $M_n$, $M_w$, $M_z$ and d (the polydispersity) are defined by the equations detailed below. $w_i$ is the weight of i molecules with molecular weight $M_i$, $N_i$ is the number of ith molecules with molecular weight $M_i$, and a is the exponent of the Mark-Houwink equation. By definition $M_n<M_w<M_z$. A d value close to unity indicates that the polymer has a narrow molecular weight distribution.

$$M_n = \frac{\sum w_i}{\sum N_i} = \frac{\sum (N_i M_i)}{\sum N_i} \quad M_w = \frac{\sum (w_i M_i)}{\sum w_i} = \frac{\sum (N_i M_i^2)}{\sum (N_i M_i)}$$

$$M_z = \frac{\sum (N_i M_i^3)}{\sum (N_i M_i^2)} \quad\quad d = \frac{M_w}{M_n}$$

The antibacterial properties of selected fibres were also investigated, and are detailed in Table 8, since the aim of significant chitosan incorporation into the alginate fibre is to impart antibacterial activity to the fibre. Shake flask testing was performed (according to ASTM E2149-01 Standard Test Method for Determining the Antimicrobial Activity of Immobilized Antimicrobial Agents under Dynamic Contact Conditions). Bacterial reduction (in terms of live bacterial cell count) following inoculation with *Staphylococcus aureus* (a well known Gram-positive bacterial inhabitant of colonised or infected wounds) was measured over a period of 0-24 hours in:

(i) flasks containing fibres suspended in buffer
(ii) flasks in (i) having had their fibres removed after initial testing
(iii) flasks containing fresh buffer containing dried fibres removed from (i)

These results show that alginic acid fibres treated with a 3% hydrolysed chitosan bath solution give the most timely and effective bacterial reduction with initial use (i.e. likely when first applied to a wound). However, alginic acid fibres treated with a 1% hydrolysed chitosan bath solution are nearly as effective initially as the 3%, and are more effective at leaching antibacterial components, presumably hydrolysed chitosan fragments (test condition (ii)). All of the re-used fibres are still capable of imparting good antibacterial properties (test condition (iii)). The slower antibacterial properties associated with the fibre treated with the 0% chitosan bath (compared to fibres treated with hydrolysed chitosan) will be due to the acidity of the fibres. In comparison, the chitosan and hydrolysed chitosan solutions that have been dialysed to neutrality clearly show the time release antibacterial effect of the chitosan. The antibacterial effect of dialysed hydrolysed chitosan is more rapid than unhydrolysed chitosan, presumably because the bacteria must first break down the latter material.

Alginic acid fibres treated with hydrolysed chitosan solution (1-5% w/v) have excellent immediate and sustained antibacterial properties.

TABLE 8

| Sample/ IncubationTime | (i) Original fibres (% Reduction) | (ii) Re-used solution after fibre removal (% Reduction) | (iii) Re-use of fibres (% Reduction) |
|---|---|---|---|
| Alginic acid + hydrol. chitosan (0%) fibre | | | |
| 1 hr | 95.87 | >99.90 | 99.30 |
| 3 hrs | >99.86 | >99.90 | >99.97 |
| 6 hrs | >99.99 | >99.90 | >99.97 |
| 24 hrs | >99.99 | >99.90 | >99.97 |
| Alginic acid + hydrol. chitosan (1%) fibre | | | |
| 1 hr | 99.61 | >99.92 | 99.52 |
| 3 hrs | >99.99 | >99.92 | >99.97 |
| 6 hrs | >99.99 | >99.92 | >99.97 |
| 24 hrs | >99.99 | >99.92 | >99.97 |
| Alginic acid + hydrol. chitosan (2%) fibre | | | |
| 1 hr | 99.91 | >99.87 | 98.57 |
| 3 hrs | >99.99 | >99.87 | >99.97 |
| 6 hrs | >99.99 | >99.87 | >99.97 |
| 24 hrs | >99.99 | >99.87 | >99.97 |
| Alginic acid + hydrol. chitosan (3%) fibre | | | |
| 1 hr | 99.98 | >99.84 | 99.09 |
| 3 hrs | >99.99 | >99.84 | >99.97 |
| 6 hrs | >99.99 | >99.84 | >99.97 |
| 24 hrs | >99.99 | >99.84 | >99.97 |
| Alginic acid + hydrol. chitosan (5%) fibre | | | |
| 1 hr | 92.33 | 91.39 | 96.60 |
| 3 hrs | >99.99 | >99.98 | 99.94 |
| 6 hrs | >99.99 | >99.98 | >99.97 |
| 24 hrs | >99.99 | >99.98 | >99.97 |
| Dialysed chitosan solution | | | |
| 1 hr | 78.08 | | |
| 3 hrs | 86.76 | | |
| 6 hrs | 89.37 | | |
| 48 hrs | 99.99 | | |
| Dialysed hydrolysed chitosan solution | | | |
| 1 hr | 88.48 | | |
| 3 hrs | 98.32 | | |
| 6 hrs | 99.47 | | |
| 48 hrs | 99.99 | | |

Shake Flask Testing on Chitosan Alginate Fibres against *S. aureus*

Initial Inoculum in each flask of *S. aureus* at 0 hour=660,576 (618)=$4.64 \times 10^6$

TABLE 9

| Product | Time | Mean Number of Microorganisms remaining from flask 1 and 2. (cfu/flask). | Percentage Reduction/ Flask |
|---|---|---|---|
| Chitosan Alginate Fibres - 3.9% Chitosan (3 h hydrolysis) (SHB1/196) | 1 h | $1.99 \times 10^5$ | 95.71% |
| | 3 h | $1.82 \times 10^4$ | 99.61% |
| | 6 h | 562.5 | 99.99% |
| | 24 h | <375 | >99.99% |
| Chitosan Alginate Fibres - 3.9% Chitosan (6 h hydrolysis) (SHB1/200) | 1 h | $1.09 \times 10^6$ | 76.51% |
| | 3 h | $2.12 \times 10^5$ | 95.43% |
| | 6 h | $1.13 \times 10^4$ | 99.76% |
| | 24 h | <375 | >99.99% |
| Chitosan Alginate Fibres - 3.9% Chitosan (9 h hydrolysis) (SHB1/204) | 1 h | $1.37 \times 10^5$ | 97.04% |
| | 3 h | <375 | >99.99% |
| | 6 h | <375 | >99.99% |
| | 24 h | <375 | >99.99% |
| Chitosan Alginate Fibres - 3.9% | 1 h | $6.13 \times 10^5$ | 86.79% |

TABLE 9-continued

| Product | Time | Mean Number of Microorganisms remaining from flask 1 and 2. (cfu/flask). | Percentage Reduction/ Flask |
|---|---|---|---|
| Chitosan | 3 h | $8.81 \times 10^3$ | 99.81% |
| (12 h hydrolysis) (SHB1/208) | 6 h | <375 | >99.99% |
|  | 24 h | <375 | >99.99% |
| Chitosan Alginate Fibres - 3.9% | 1 h | $7.84 \times 10^5$ | 83.10% |
| Chitosan | 3 h | $6.00 \times 10^4$ | 98.71% |
| (15 h hydrolysis) (SHB1/212) | 6 h | $2.44 \times 10^3$ | 99.95% |
|  | 24 h | <375 | >99.99% |

Conclusion: Chitosan-alginate fibres incorporating chitosan subjected to 9 hours hydrolysis have the most effective antimicrobial kill.

It is of course to be understood that the present invention is not intended to be restricted to the above embodiments which are described by way of example only.

The invention claimed is:

1. A wound management fibre for releasing chitosan, chitin or chitan, comprising:
   a base fibre having a chitosan, chitin or chitan material associated therewith, the chitosan, chitin or chitan material being disrupted to provide 1 to 30% by weight of chitosan, chitin or chitan fragments of reduced molecular weight, wherein the base fibre is enabled to release the chitosan, chitin or chitan, wherein the chitosan, chitin or chitan material provides an outer coating layer for the base fibre.

2. A wound management fibre according to claim 1, wherein the chitosan, chitin or chitan material penetrates the base fibre at least to an extent.

3. A wound management fibre according to claim 1, characterised in that; at least some amount of chitosan, chitin or chitan material penetrates the base fibre.

4. A method for the production of a wound management fibre for releasing chitosan, chitin or chitan, comprising the steps of:
   extruding a base fibre;
   treating said base fibre with a chitosan, chitin or chitan material in the absence of free calcium ions, such that the chitosan, chitin or chitan material forms an association with the base fibre, and the chitosan, chitin or chitan material being disrupted to provide 1 to 30% by weight of chitosan, chitin or chitan fragments of reduced molecular weight, wherein the base fibre is enabled to release the chitosan, chitin or chitan; and
   disrupting the chitosan, chitin or chitan material prior to the treatment of the base fibre such that the chitosan, chitin or chitan material comprises chitosan, chitin or chitan fragments of reduced molecular weight, wherein the base fibre is treated with the chitosan, chitin or chitan material having a concentration in the range from 2.5 to 5.0% w/v.

* * * * *